United States Patent
Kadash et al.

Patent Number: 5,885,237
Date of Patent: *Mar. 23, 1999

[54] TRIMMABLE WOUND DRESSING

[75] Inventors: Marjory A. Kadash, Skillman, N.J.; Harry B. Friggle, Greensboro, N.C.

[73] Assignee: Bristol-Myers Squibb Company, Skillman, N.J.

[*] Notice: This patent issued on a continued prosecution application filed under 37 CFR 1.53(d), and is subject to the twenty year patent term provisions of 35 U.S.C. 154(a)(2).

[21] Appl. No.: 624,758

[22] Filed: Mar. 27, 1996

Related U.S. Application Data

[63] Continuation of Ser. No. 131,807, Oct. 5, 1993, abandoned.

[51] Int. Cl.[6] ............................................. A61F 13/00
[52] U.S. Cl. ........................... 602/48; 602/41; 602/56; 424/445
[58] Field of Search ........................... 602/41–43, 46, 602/48, 49, 57–60, 903; 206/438, 440, 441; 604/304, 309, 368, 904; 424/445, 446, 447

[56] References Cited

U.S. PATENT DOCUMENTS

| | | | |
|---|---|---|---|
| 2,508,855 | 5/1950 | Brown | 602/903 |
| 3,143,208 | 8/1964 | Sizemore | 602/903 |
| 3,604,421 | 9/1971 | Pizzella . | |
| 3,665,920 | 5/1972 | Davis | 128/287 |
| 3,853,598 | 12/1974 | Raguse | 602/903 |
| 4,252,120 | 2/1981 | Carpenter . | |
| 4,327,728 | 5/1982 | Elias | 604/368 |
| 4,427,737 | 1/1984 | Cilento et al. | 602/903 |
| 4,538,603 | 9/1985 | Pawlechak et al. . | |
| 4,551,490 | 11/1985 | Doyle et al. . | |
| 4,728,642 | 3/1988 | Pawelchak et al. | 602/48 |
| 4,773,409 | 9/1988 | Cilento et al. | 602/49 |
| 4,909,243 | 3/1990 | Frank et al. | 128/156 |
| 4,952,618 | 8/1990 | Olsen | 524/17 |
| 5,213,565 | 5/1993 | Rollband | 602/42 |
| 5,264,218 | 11/1993 | Rogozinski | 602/41 |
| 5,369,155 | 11/1994 | Asmus | 525/55 |
| 5,397,298 | 3/1995 | Mazza et al. | 602/903 |
| 5,416,205 | 5/1995 | Della Valla et al. | 602/49 |
| 5,429,589 | 7/1995 | Cartmell et al. | 602/42 |
| 5,478,308 | 12/1995 | Cartmell et al. | 602/57 |
| 5,603,946 | 2/1997 | Constantine | 424/445 |

FOREIGN PATENT DOCUMENTS

| | | | |
|---|---|---|---|
| 9300056 | 1/1993 | Denmark . | |
| 0164319 | 12/1985 | European Pat. Off. | 602/58 |
| 0547833 | 6/1993 | European Pat. Off. . | |
| 2249266 | 5/1992 | United Kingdom | 602/46 |
| 9213713 | 8/1992 | WIPO . | |

Primary Examiner—Ronald Stright, Jr.
Assistant Examiner—A. T. Nguyen
Attorney, Agent, or Firm—John M. Kilcoyne; Theodore R. Furman, Jr.

[57] ABSTRACT

This invention relates to improved wound dressings that are adapted to being readily sized to fit the shape of the wound so that healing is promoted. In particular, the present invention is directed to a scored spiral wound dressing. More particularly, this invention relates to a spiral wound dressing having superior absorption properties and which is capable of swelling in the presence of wound fluid to closely fit the wound.

20 Claims, 2 Drawing Sheets

TRIMMABLE WOUND DRESSING

This application is a continuation of U.S. patent application Ser. No. 08/131,807, filed Oct. 5, 1993, now abandoned.

FIELD OF THE INVENTION

This invention relates to improved wound dressings that are adapted to being readily sized to fit the shape of the wound so that healing is promoted. In particular, the present invention is directed to a scored spiral wound dressing. More particularly, this invention relates to a spiral wound dressing having superior absorption properties and which is capable of swelling in the presence of wound fluid to closely fit the wound.

BACKGROUND OF THE INVENTION

It is recognized that providing a dressing that promotes healing without scab formation is desirable in wound treatment. In addition, the removal of excess wound exudates is important to promote wound healing and to prevent the breakdown of skin surrounding the wound due to maceration.

Many different types of dressings are commercially available. These commonly include dressings containing gauze, foams, sponges, cotton, wools or other fibrous materials. Gauze and other fibrous materials, while capable of absorbing wound exudate can create problems in wound care because of the tendency of these fibrous materials to be engulfed or entrapped by the newly formed tissue that grows into the dressing. As a result, when these fibrous wound dressings are removed newly formed tissues can be damaged and torn. The other commonly used materials for removing exudates in wound dressings include granules and pastes. Similarly, these are frequently difficult to remove from the wound after hydration by the exudate and typically require flushing with a liquid. Further, these materials are limited in the amount of exudate they can absorb.

U.S. Pat. No. 4,551,490 describes an adhesive composition useful with ostomy and incontinent appliances and which has also been used in adhesive bandages. The composition consists of a homogeneous mixture of polyisobutylene, styrene random or block-type copolymer, mineral oil, soluble hydrocolloid gum, water swellable cohesive strengthening agent and a tackifier. This composition has limited exudate absorption capacity and requires a tackifier for its intended use as an adhesive composition.

U.S. Ser. No. 990,719 filed Dec. 15, 1992 which is commonly owned by the assignee of the present invention teaches improved wound fillers having high absorption capabilities. The wound filler is preferably comprised of from about 25% to 75% by weight of a polymer matrix and 25% to 75% by weight absorbing powers. The disclosures of this application are incorporated herein by reference.

SUMMARY OF THE INVENTION

The present invention is directed to an improved dressing material in the form of a thin wafer or disc. The wafer is provided with a score line or separation line to facilitate the unraveling of the disc or wafer to provide a strand or rope of dressing material for wound management which may involve wound filling and/or covering. In addition, if desired the dressing may be used as a wafer that can be trimmed to the size of the wound by the use of the score line usually without the need for a cutting instrument. Preferably the score line is in the form of a spiral which when the wafer is unwound or separated at the score line provides a generally flat rope-like material. The rope of dressing can be used to fit the wound. The dressing is preferably made from materials which are capable of absorbing fluid or exudate and which may also swell when moistened. The dressing maintains cohesion upon absorption and can be removed as a single unit.

DETAILED DESCRIPTION OF THE INVENTION

Figure 1:
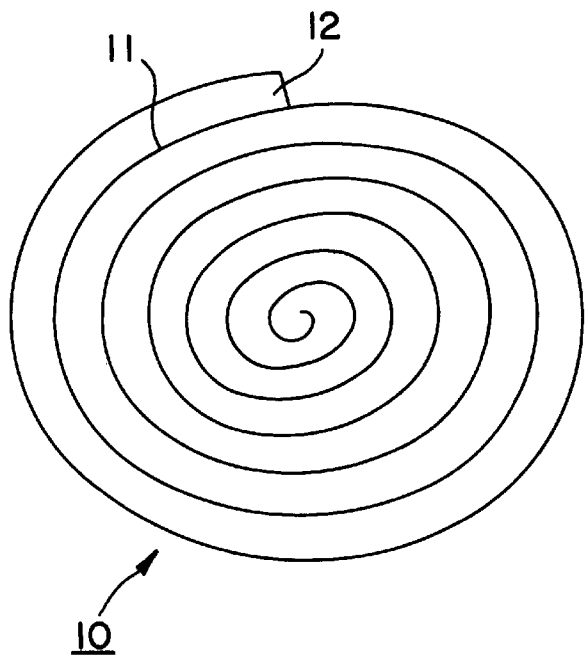
FIG. 1 is a top view of one embodiment of the dressing of the present invention.
Figure 2:
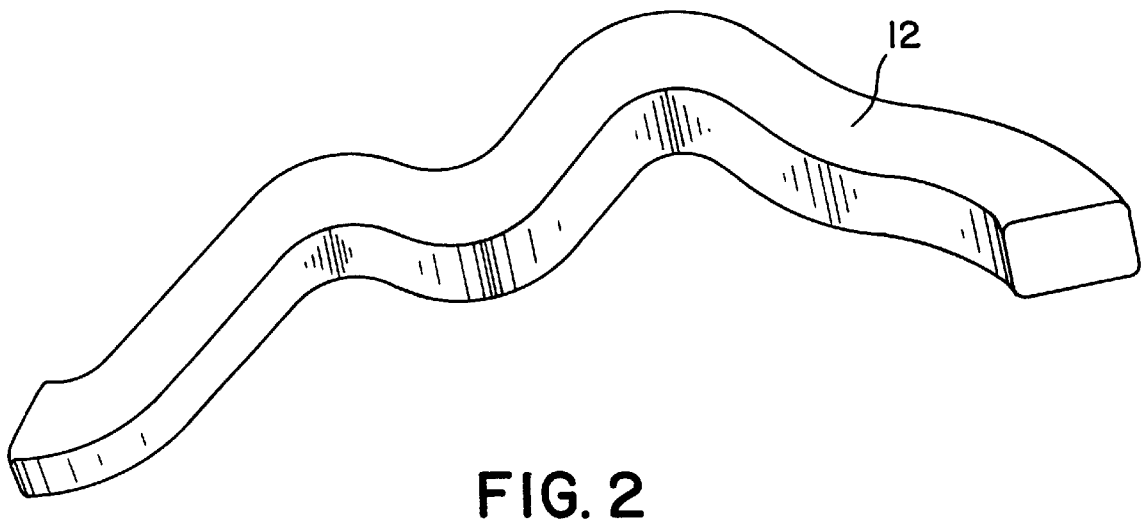
FIG. 2 is a 3-dimensional view of one embodiment of a segment of rope obtained by unraveling from a disc of the present invention.
Figure 3:
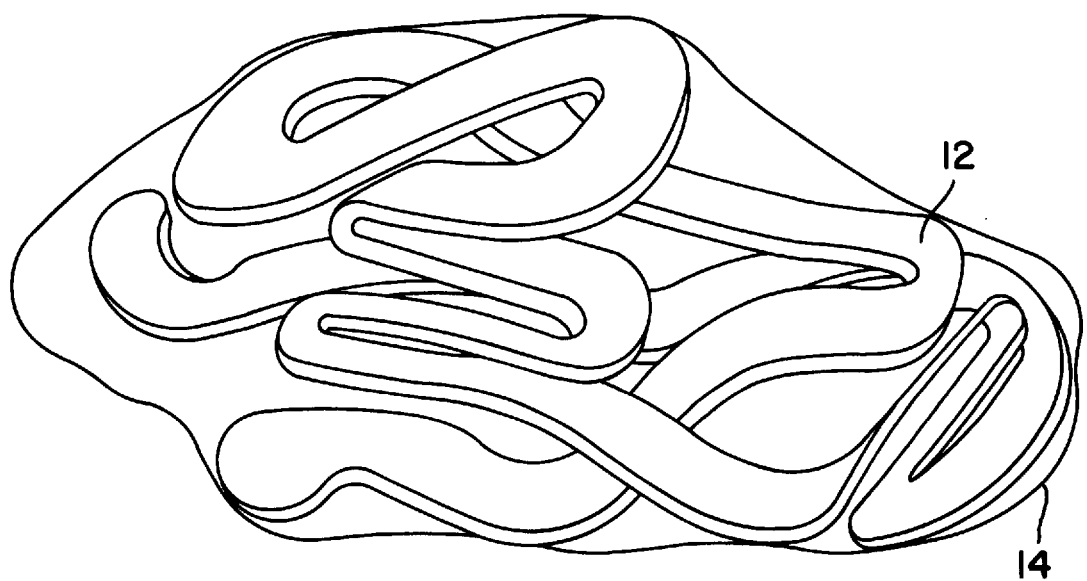
FIG. 3 is a top view of one embodiment of the rope filling an irregularly shaped wound.

As shown in FIG. 1 the present invention is a dressing in the form of a wafer 10 that is generally a thin flat disc. While the diameter or the dimensions of the upper surface may vary in size depending on the intended wound size, the thickness of the wafer is preferably under about ¼". As seen in FIG. 1 the dressing may be circular or even oblong in shape. The disc is provided with at least one score line 11 or area of weakness which permits the dressing to be unwound to form a rope of the dressing material. In many instances, for example, for the treatment of irregular shaped wounds, the rope is preferably unraveled or trimmed from the disc and the desired amount of such removed-rope can be applied to, or inserted into, the wound itself. This facilitates application to the wound and improves wound coverage. Cross sectionally the rope can be of any convenient configuration. Preferably, the rope has a generally rectangular cross-section. As seen in FIG. 2 the dressing of the present invention can be in the form of a rope. In FIG. 3 this rope 12 is shown applied to an irregular shaped wound 14. In addition, if so desired, the wafer can be used either in its entirety or with a portion of the rope removed so as to tailor the size of the dressing to the wound. In either event, the dressing unravels upon absorption of wound exudate and conforms to the aperture of the wound. When the rope is to be unraveled by the caregiver prior to application to the wound, the rope may be manually trimmed from the disc. Trimming or unraveling may be accomplished by hand or by any suitable instrument.

The score line is preferably spiral in its orientation. A spiral score line in the dressing permits the dressing to be unwound to form a continuous rope of dressing material which can fit the wound's general dimensions facilitating wound coverage by the dressing.

As shown in FIG. 3 the dressing of FIG. 1 has been unraveled so that the resulting rope fits within the wound 14. Unraveling may be accomplished by merely applying force at the score line to separate the section 12 from the remainder of the dressing or by use of a suitable cutting means. The dressing in the form of a rope may be trimmed to any desired length.

The dressing of the present invention is formed of a material that possesses good exudate absorption, and preferably contains one or more hydrocolloids. Typically, presently available materials of this sort may swell to several times their original size when in contact with a moist environment. One attribute of the dressing of the present invention is that when it swells, the dressing has the tendency to retain its original cross sectional shape. Thus, if the dressing originally has a rectangular cross section when the dressing comes into contact with fluid it expands to several times its original size but still retains its rectangular cross section. It is believed that this cross-sectional shape may contribute to the wound healing improvement provided by the present invention.

By providing a dressing that is swellable, more complete coverage of the wound is possible. Indeed, the wound need not be completely filled at initial application, because the swellable material will increase in dimension to fill the wound upon exposure to exudate. This is especially useful when using a rope in irregularly shaped wounds. Alternatively, if the hydrocolloid-containing dressing material is in the form of a foam (rope or disc), it can possess suitable absorption properties with little or no increase in its dimensions. In situations where it is desirable to completely fill the wound upon initial application, this embodiment will be preferred. As will be appreciated, the dressing of the present invention is trimmed along the score line to form a rope which can be applied to fit the general configuration of the wound. Whatever small gaps in the dressing's coverage of the wound are readily reduced or eliminated as the dressing becomes moist and expands.

TABLE

| Prior Art Wound Fillers | Drawbacks | Present Spiral Dressing |
|---|---|---|
| 1. Gauze soaked in saline | dries out; tissue in-growth | stays moist; no in-growth |
| 2. Alginate fibers | form gel which must be flushed out for removal; may dry out | stays moist; maintains its integrity for complete removal |
| 3. Gels | liquify, must be flushed out; cannot accommodate much exudate | handles high degree of exudate |

The dressing of the present invention may be formed of any suitable material that provides good exudate absorption and preferably contains one or more hydrocolloids. A preferred material for use as the dressing of the present invention is a wound filler comprising from about 25% to 75% by weight of a polymeric matrix and 25% to 75% by weight of absorbing powders. Preferably, the wound filler contains about 35% to 50% matrix and about 50% to about 65% absorbing powders.

The polymer matrix may preferably contain about 15% to 75% of one or more styrene random or block type copolymers, from about 5% to 40% by weight of one or more polyisobutylenes and from 5% to 40% by weight of mineral oil.

The absorbing powders include, but are not limited to, sodium or calcium alginates, cross-linked sodium carboxymethyl cellulose, absorbent polyacrylates and water soluble hydrocolloids.

The hydrocolloid materials useful in the present invention include any water soluble gum such as pectin, gelatin, guar gum, locust bean gum, gum karaya, carboxymethylcellulose (CMC), sodium/calcium alginate fibers, polysaccharides and the like and mixtures thereof. The absorbing powders may also contain additional materials such as antibodies, or growth factors, and silver sulfadiazine or other antibacterial products. The hydrocolloid may contain other additives and agents. Suitable antibiotic or antimicrobial agents including neomycin and penicillin may be used. A suitable antiseptic agent is povidone iodine. Suitable antiinflammatory agents include hydrocortisone and triamcinolone acetonides. A skin protective agent, such as zinc oxide, may also be included in the mixture. The hydrocolloid may be present in the powder, either with or without accelerators, to promote release, such as surfactants. The hydrocolloids are present in an amount of from about 0% to 75% of the weight and preferably 5% to 15%.

The styrene random or block copolymer of the matrix permits the swelling of the absorbent powders while maintaining cohesion. Suitable styrene copolymers include styrene-butadiene-styrene (S-B-S) and styrene-isoprene-styrene (S-I-S) block copolymers which are available from Shell Chemical Co. under the trademark Kraton i.e. Kraton D1100, 1101, 1102, 1107 etc. The most preferred material is the styrene-isoprene-styrene copolymer Kraton D1107. Blends of styrene-isoprene-styrene (S-I-S) copolymers either alone or with SBS copolymers may also be used. In addition, there may be blends of one or more SBS copolymers.

The presence of polyisobutylene in the wound filler aids in binding the absorbing powders in the styrene network. Preferred polyisobutylenes are lower molecular weight polyisobutylene having a viscosity average molecular weight of from about 36,000 to about 58,000 (Florey). Such polyisobutylenes are commercially available under the trademark Vistanex from Exxon as grades LMMS and LMMH. Preferably, the polyisobutylene, Vistanex LMMH is used in the wound filler of this invention. If desired, 25% to 75% of the polyisobutylene can be substituted with butyl rubber.

The mineral oil functions as a plasticizer for the styrene random or block copolymer component. It also functions to increase the stretchability of the wound filler matrix.

The absorbing powders of the wound filler of the present invention constitute 25% to 75% by weight of the composition. In the preferred compositions, the absorbing powders are present in about 50% to 65% by weight. The powders for use in this invention absorb at least 300% by weight of the wound filler and preferably 500%. The absorbing powders useful in the invention have large water absorbing capacity, i.e., 1000% to 4000% by weight and are capable of being irradiated without substantial loss of water absorbing capacity. Additionally, they must not be easily leached out of the matrix when in contact with water.

Alginate-containing absorbent powders are known such as those available under the tradename KELSET from Kelco Co., or mixtures of sodium alginate and calcium alginate commercially available under the tradename SOBALG Na Alginate and SOBALG Ca Alginate and commercially available from Grinsted of Denmark or mixtures of Na Alginate and Ca Alginate available under the tradenames PROTANAL Na Alginate and PROTANAL Ca Alginate from Protan of Norway. Preferably, the absorbing powders contain 10% to 75% by weight of sodium-calcium alginates.

Absorbing powders such as cross-linked sodium carboxymethyl cellulose are commercially available under the tradename AcDiSol from FMC and under the tradename AKUCELL SWX 177 from Akzo Co. of Holland. The powders may also include finely divided substantially water insoluble, highly absorbent polyacrylates. Representative of the highly absorbent polyacrylates are starchgraft copolymer such as that described in U.S. Pat. No. 3,661,815 and commercially available from Grain Processing Corp. under the tradename WATER LOCK [a starch-graftpoly (sodium acrylate-co-acrylamide)], salt of cross linked polyacrylic acid/polyalcohol grafted copolymer commercially available under the tradename FAVOR SAB800 from Stockhausen, Inc. Greensboro, N.C., polyacrylate available under the tradename SALSORB 84 from Allied Colloids, Inc. Suffolk, Va., sodium polyacrylate available under the tradename WATER LOCK J500 from Grain Processing Corporation, cross-linked acrylic polymer under the name ARIDALL 1078 from American Colloid Company, Skokie, Ill., and potassium polyacrylate under the name ARASORB 732 and 810 from Arakawa Chemical Industries, Ltd., Osaka, Japan. WATER LOCK A140 is the preferred polyacrylate.

The wound filler of this invention may be prepared by mixing the components in a heated, sigma blade, kneader mixer. The batch components are kneaded for a prescribed length of time in the temperature controlled mixer. When mixing is complete, the batch is discharged using the extrusion screw at the base of the mixer. The formulated means is fed to the hopper of a single screw extruder. The extruder heats and pumps the mass along the extruder barrel and through a sheet forming die. The mass is calendared to the desired thickness and wound on a take-up roll. Rolls of extruded material are cut to the desired shape and size by passing the sheet through a rotary die cutter. The score line may be formed by any suitable means including, for example, manually such as by a blade or by means of laser scoring. No matter the method of forming the area of weakness, care must be taken to avoid creating too deep a score line that unnecessarily weakens the dressing. The dressings are then individually sealed in appropriate packaging and terminally sterilized.

EXAMPLE

An absorbent wound filler was prepared having the following composition:

Polyisobutylene (Vistanex LMMH) 11.25 kg

Styrene-isoprene-styrene copolymer (Kraton D-1107) 22.5 kg

Mineral Oil 11.25 kg pectin 10 kg

NaCa Alginate (Kelset) 15 kg

Starch graft copolymer (Water Lock A-140) 30 kg

The Vistanex LMMH was added to a sigma blade mixer preheated to 305° F. and mixed for ten minutes. The Kraton was pre-melted and mixed for ten minutes. The mineral oil was added to the plastic mass in three separate allotments with ten minutes mixing after each allotment. The mass was mixed an additional 30 minutes to ensure full incorporation of the oil into the plastic mass. The powders were added next with four to five minutes mixing after the addition of each powder. At the completion of mixing, the mass temperature was 220° F.

The mass was removed from the mixer as a crumb which was fed into a 2½" single screw extruder. Extruder temperatures ranged from 225° F. to 250° F. The mass was extruded through a sheet die and calendared between silicone release paper to a thickness of 85 mils. The calendared mass was wound on a roll and then proceeded to a rotary die cutting process. Spiral disks 49 to 60 mm in diameter were cut from the mass sheet. The spiral dressings were individually packaged in film/paper chevron pouches and terminally sterilized by gamma irradiation at 2.7 to 3.3 Mrads.

When the absorbent wound filler of this example was tested for moisture absorption (on a saline soaked sponge), the following results were obtained.

| Absorbency of Spiral Shaped Dressing | | | | | | |
|---|---|---|---|---|---|---|
| time (hours) | 0 | 2 | 4 | 6 | 24 | 48 |
| average gain per square inch (grams) | 0 | 3.2 | 4.7 | 6.0 | 14.3 | 18.7 |
| percent | 0 | 85 | 145 | 200 | 539 | 721 |

The dressing of the present invention provides an excellent degree of wound debridement and in a preferred embodiment is capable of swelling to several times its original size usually at least 2 to 4 times its original size. In addition, the dressing remains moist and is easily removed from the wound.

What is claimed is:

1. A wound dressing comprising a wafer of wound exudate absorbent dressing material, said wafer having at least one area of weakness along a surface so that a portion of said wafer is separable from the remainder of said wafer to form a rope of dressing material sizable to fit the shape of a wound, the remainder of said wafer staying intact.

2. The wound dressing according to claim 1 wherein said area of weakness is a score line.

3. The wound dressing according to claim 2 wherein said score line forms a spiral.

4. The wound dressing according to claim 3 wherein said wafer is swellable with exudate to at least twice its original size.

5. The wound dressing according to claim 4 wherein said wafer is swellable with exudate to about 2 to 4 times its original size.

6. The wound dressing according to claim 5 wherein a portion of said wafer is separated from the remainder of said wafer to form a rope which retains its cross-section upon swelling with exudate.

7. The wound dressing according to claim 6 wherein said rope is rectangular in cross-section.

8. The wound dressing of claim 1 wherein the wafer is foam.

9. The wound dressing of claim 1 wherein the wafer does not increase in size upon absorption of exudate.

10. A wound dressing comprising a wafer of wound exudate absorbent dressing material, said wafer having at least one score line along a surface so that a portion of said wafer is separable from the remainder of said wafer to form a spiral rope of dressing material sizable to fit the shape of a wound, the remainder of said wafer staying intact, and said wafer having a moisture absorbency of at least 300% by weight.

11. The wound dressing according to claim 10 wherein said dressing is comprised of about 25% to about 75% by weight of a polymeric matrix and from about 25% to about 75% by weight of absorbing powders.

12. The wound dressing according to claim 11 wherein said dressing is comprised of about 35% to about 50% by weight of a polymeric matrix and from about 50% to about 65% by weight of absorbing powders.

13. The wound dressing according to claim 12 wherein said polymeric matrix comprises from about 15% to about 75% by weight of a styrene copolymer, about 5% to about 40% by weight of at least one polyisobutylene and from about 5% to about 40% by weight of a plasticizer.

14. The wound dressing according to claim 13 wherein said absorbing powder is selected from the group consisting of alginates, cross-linked sodium carboxymethyl cellulose, absorbent polyacrylates, water soluble hydrocolloids and mixtures thereof.

15. The wound dressing according to claim 14 wherein said styrene copolymer is styrene-butadiene-styrene.

16. The wound dressing according to claim 14 wherein said styrene copolymer is styrene-isoprene-styrene.

17. The wound dressing according to claim 14 wherein said plasticizer is mineral oil.

18. The wound dressing according to claim 14 wherein said dressing has been irradiated.

19. The wound dressing according to claim 14 wherein said absorbing powder includes sodium alginate.

20. The wound dressing according to claim 14 wherein said absorbing powder includes calcium alginate.

* * * * *